United States Patent
Efthimiou

(10) Patent No.: US 8,978,654 B2
(45) Date of Patent: Mar. 17, 2015

(54) PERSONAL AIR FILTER WITH AMPLIFIER AND VIBRATOR

(76) Inventor: Dimitrios Efthimiou, Wheelers Hill (AU)

( * ) Notice: Subject to any disclaimer, the term of this patent is extended or adjusted under 35 U.S.C. 154(b) by 702 days.

(21) Appl. No.: 12/746,804

(22) PCT Filed: Dec. 8, 2008

(86) PCT No.: PCT/AU2008/001808
§ 371 (c)(1),
(2), (4) Date: Jun. 8, 2010

(87) PCT Pub. No.: WO2009/070851
PCT Pub. Date: Jun. 11, 2009

(65) Prior Publication Data
US 2010/0268131 A1    Oct. 21, 2010

(30) Foreign Application Priority Data
Dec. 8, 2007  (AU) ................. 2007906664

(51) Int. Cl.
A62B 7/10   (2006.01)
A62B 23/02  (2006.01)
A63B 23/18  (2006.01)

(52) U.S. Cl.
CPC  *A62B 7/10* (2013.01); *A63B 23/185* (2013.01)
USPC ............ 128/205.29; 128/205.27; 128/200.24

(58) Field of Classification Search
USPC ............ 128/205.27, 205.29, 200.24, 201.25, 128/205.28, 206.12, 206.16, 206.17; 601/47; 181/175; 55/310
See application file for complete search history.

(56) References Cited

U.S. PATENT DOCUMENTS

| 3,715,448 | A | | 2/1973 | Itoh | |
|---|---|---|---|---|---|
| 3,731,678 | A | * | 5/1973 | Pyzel | 128/202.26 |
| 4,387,784 | A | | 6/1983 | Hill | |
| 5,315,987 | A | | 5/1994 | Swann | |
| 5,524,616 | A | * | 6/1996 | Smith et al. | 128/205.27 |
| 5,690,101 | A | | 11/1997 | Kutta | |
| 5,771,885 | A | * | 6/1998 | Putrello | 128/205.27 |

(Continued)

FOREIGN PATENT DOCUMENTS

| GB | 2401474 B | 5/2005 |
|---|---|---|
| RU | 2190955 C2 | 10/2002 |
| SU | 904662 A1 | 2/1982 |
| WO | 2006059340 A1 | 6/2006 |

OTHER PUBLICATIONS

Cullum, The Practical Application of Acoustic Principles, Chapter One "The Nature of Noise", Published in 1949, pp. 15-27, 14 Pages.

(Continued)

*Primary Examiner* — Justine Yu
*Assistant Examiner* — Colin W Stuart
(74) *Attorney, Agent, or Firm* — Brooks Kushman P.C.

(57) ABSTRACT

A personal air filter device having a housing defining a cavity and a central opening including a first and second vent. The device also includes a mouthpiece adjacent to the second vent and spaced apart from the central opening. The device has a filter within the housing for filtering air passing through the housing when inhaling and exhaling. The cavity resonates at audible frequencies for providing respiratory feedback when a user inhales or exhales.

13 Claims, 1 Drawing Sheet

(56) References Cited

U.S. PATENT DOCUMENTS

| | | | |
|---|---|---|---|
| 6,345,617 B1* | 2/2002 | Engelbreth et al. | 128/200.23 |
| 6,550,479 B1 | 4/2003 | Duxbury | |
| 7,025,060 B1* | 4/2006 | Nicholson | 128/206.29 |
| 2003/0075173 A1 | 4/2003 | Shahaf | |
| 2003/0234016 A1 | 12/2003 | Swann | |
| 2004/0007234 A1 | 1/2004 | Duxbury | |
| 2004/0089303 A1 | 5/2004 | Chien | |
| 2004/0118397 A1 | 6/2004 | Swann | |
| 2008/0035151 A1* | 2/2008 | Solorzano-Garcia | 128/206.11 |

OTHER PUBLICATIONS

International Search Report for PCT/AU2008/001808, Completed by the Australian Patent Office on Jun. 1, 2009, 5 Pages.

Written Opinion of the International Searching Authority for PCT/AU2008/001808, Completed by the Australian Patent Office on May 11, 2009, 3 Pages.

International Preliminary Report on Patentability for PCT/AU2008/001808, Completed by the Australian Patent Office on Mar. 17, 2010, 8 Pages.

* cited by examiner

PERSONAL AIR FILTER WITH AMPLIFIER AND VIBRATOR

BACKGROUND OF THE INVENTION

1. Field of Invention

This invention generally relates to personal air filters, and specifically, to a personal air filter with amplifier and vibrator.

2. Prior Art

Air, and thereby breathing, is fundamental to life. Air purification has long been a concern for industrial situations, and is now increasingly becoming a concern for personal situations. Due to industrial biohazard and viral contamination problems, respiratory protective devices such as respiratory gas masks and surgical masks have long been used in workplace and emergency biohazard settings. While these devices are very effective for those professionals that wear them, their bulk and conspicuousness can be a deterrent to the private individual. Due to personal health concerns, individuals in today's health-conscious and active society are increasingly seeking to breathe purer air in personal settings, such as to reduce exposure to pollen or other airborne particulates or microorganisms. This is usually achieved outdoors by wearing surgical masks or indoors by electronic devices such as air purifiers. However such use is not widespread due to conspicuousness of wearing the masks or impracticality of transporting electronic air purifiers and ineffectiveness of using them in large unconfined spaces.

Existing protective inhalation masks currently available have a number of drawbacks, including that they are cumbersome and unattractive, they make communication more difficult because they cover the mouth, partially obstruct the view of the wearer, and can be uncomfortable to wear due to their method of attachment to the head, mouth, nose, or ears. Further, they are inconvenient because they do not lend themselves to instant usage by being readily put on and taken off, are unattractive and make users conspicuous, and are better suited for use in an industrial setting, rather than during, day-to-day and leisure activities.

Furthermore, the relation between physiological conditions with physical, mental and emotional health has, also become increasingly important given the growing complexity of life and preoccupation with wellness. Ancient civilizations and modern studies have shown that stress and other emotional factors increase the risk of disease, reduce performance and severely restrict quality of life. This has led to increasing awareness and interest in practices such as yoga and tai chi to optimize respiration and circulation for promoting health and fitness. According to the traditions of such practices, a person can achieve good health and longevity through controlled breathing, otherwise described as "abdominal breathing", which is a system of exercise involving extensive training and discipline. The most common but less effective respiration process is "thoracic breathing" whereby air is inhaled and exhaled at the thoracic level. A less common yet more effective respiration process is "abdominal breathing" whereby air is inhaled and exhaled at the abdominal level, which has been practiced by yoga adherents for millennia enjoying the benefits of better quality of life and longevity of life.

Yoga, tai chi and the like, utilize certain body postures to stimulate and internally massage the body. Such physical exercise is designed to remove blockages and constraints from body organs and interconnections in order to optimize circulation. In particular, yoga physical exercise intimately combines body postures with abdominal breathing. However, unlike body posture exercises, where the mind readily concentrates on the physical pose due to its tangibility, for the breathing process, the mind does not readily concentrate on respiration due to its subtleness and intangibility. Yoga masters teach that controlled breathing requires the ears for mastery. This is because the mind must concentrate on the sound of breathing, with the ears providing undistracted focus, attentively listening to the rhythm, to achieve slow and regular respiration. Controlled breathing requires concentrated attention on the airflow to the abdomen, chest and thoracic area, as well as consistent duration of airflow for inhalation, retention and exhalation. Compounding the difficulty of maintaining attention on the breathing process is losing mental focus due to distraction by visual or aural stimuli. Meditation is used in Yoga exercise to aid focusing the mind for concentration. Meditation involves concentration practices, such as chanting the word 'Aum', in order to clear the mind of distractions and maintain concentration.

However, breathing is naturally quiet which makes it difficult to concentrate on the timing of airflow to the abdomen, chest and thoracic areas. Mastery of slow, deep and rhythmic inhalation and exhalation requires long periods of concerted practice and undivided attention. The duration of air flow cannot be suitably preset or programmed since it varies according to each person's lung capacity. Unless there is a completely silent and darkened environment, the mind's attention easily wanders after visual and aural distractions. Hence traditional forms of controlled breathing exercise, such as Yoga and Tai Chi are difficult to learn properly and require a level of discipline that few people can afford, unless they pay for the financial and time expense of attending regular classes instructed by a professional at a dedicated venue. There is a need for a device, and method to compliment these traditional forms of exercise. A device which amplifies respiration sensory feedback audibly and tactilely in a way that can guide and support a similar controlled breathing discipline for an average fitness enthusiast without distraction or requiring use of chanting for concentration, in order to control breathing by tracking and maintaining proper breathing duration, rate and rhythm. Prior art devices utilize bells, chimes or other audible means to signal the user to 'return' to concentration as well as an appropriate moment to change breathing stage between inhalation, retention and exhalation. However, these devices have a number of disadvantages. There is a need for a device which can facilitate the meditative state without requiring the significant amount of time and money to be spent on learning yoga theory and principles, arcane philosophies or understanding meditation practices and procedures in order to facilitate concentrated mindful controlled breathing. There is a need for a device which does not require the user to be in a silent environment lacking visual and aural distractions that may prevent the user from hearing the user's respiration Further, a device which provides user feedback without requiring cumbersome electronic devices or wires attached to the body to monitor abdominal or other respiration activity, or processing and transmitting response or predetermining and presetting timing intervals for each breathing cycle stage. Further, a device which does not require external audio or visual stimulus signal feedback, to advise a user to change breathing cycle stage. Further, a device which is naturally aspirated and does not require an external power source.

'Aum' chanting is also used to facilitate synchronizing a person's internal body vibrations with external universe vibrations. According to yoga theory, harmony in such vibrations produces optimal circulation and results in physical, mental and emotional relaxation, invigoration and wellbeing. However 'Aum' chanting requires training and supervision to ensure the proper breathing technique combined with proper vocalization. Alternative artificial means of producing the soothing effects of meditation vibration is via electro-mechanical means of oscillating parts in a device, commonly comprising a vibrator or massager, relying on electrical means to produce vibration, and requiring an electrical power source.

However, in yoga, tai chi and the like, internal massage and vibration stimulation is achieved after prolonged practice requiring close supervision of a teacher in order to guide the pupil with the correct body postures, breathing methods and "mantra" chanting. 'Aum' mantra chanting is not widely accepted due to conspicuousness, arcane philosophy as well as complexity which make it impractical in modern society due to time and financial constraints, as well as limited numbers of qualified instructors. Without advanced practice with extended know how, only electronic massagers are capable of providing vibration stimulation to the body approximating the effect produced by yoga. However, massagers have a number of disadvantages, including that they require a power source, are noisy, cumbersome, conspicuous, or external to the body causing friction and irritation to skin, disregard relevant controlled breathing, and may require external transmission media such as creams, oils or gels. There is a need for a naturally aspirated vibration device which does not rely on external electric power source, does not require transmission devices such as creams, oils or gels, and need not cause friction to the skin. Further, there is a need for a device which can transmit and communicate one person's vibrations to another facilitating educational, training, therapeutic or leisure and pleasure use.

Despite the amount of prior art, there remains a need for an easily portable pocket-sized and inexpensive simple to use personal breathing filter that optimizes breathing making it simple, easy, convenient, and inexpensive. A device that can effectively remove organic and inorganic particles from inhaled air, while not requiring increased effort by the user to maintain normal breathing. Further, that can be inconspicuously and conveniently handheld and used by individuals while going about daily activities in any indoor or outdoor environment, and will provide air filtration purification and freshening of ambient air immediately prior to inhalation. A device resonating for audibly amplifying respiration thereby facilitating concentration on proper controlled breathing inhalation, retention and exhalation process. Further, a naturally aspirated oscillating vibration massaging device stimulating blood circulation and transmission of a user's vibrations facilitating education and training, leisure and pleasure, beauty health and fitness.

Objects and Advantages

Accordingly, several objects and advantages of this invention are to provide an improved personal air filter with the advantage that it is handheld or palm-sized and instantly accessible with the advantage of inconspicuously providing immediate and temporary relief from various forms of air pollution and enhanced air.

It is a further object of the device to provide a personal air filter with High Efficiency Particulate Air characteristics with the advantage of reducing airborne particles, microorganisms, and other contaminants in user-surrounding proximate inhaled air, such as ambient odors, pollens, impurities, air pollution, dust, fungi, bacteria, viruses, and other respiratory pathogens and transient microorganisms.

Another object and advantage is that the device permits a user to conduct daily activities while providing a convenient, comfortable, portable, and inconspicuous means to inhale filtered air.

Another object and advantage is to provide a more user friendly yet economical personal air filter.

A further object and advantage is to provide means of monitoring duration of breathing inhalation, retention and exhalation.

A further object and advantage is to provide a naturally aspirated means of vibration for human energy transfer.

A further object is to monitor breathing duration, with an advantage being that user can control the breathing rate and depth, thereby achieving regular and rhythmic abdominal breathing.

Another object and advantage is to improve human physical, physiological and emotional states by using the device for sequential equivalent duration respiration cycles for optimal breathing patterns for the user leading to maintenance and improved health and fitness of body organs, glands, tissues and cells.

Still another advantage of the device is it is lightweight, compact and portable. The respiration cycle technique of using the device is simple and can be performed at home, office, or outdoors, whilst stationary, moving or traveling on public or private transport, or stationary in front of a television or when listening to music.

It is a further object of the invention to amplify respiration for aural and tactile sensory feedback in order to track and maintain controlled breathing cycle duration, rate and rhythm, with the advantage that it provides guidance and support to a practitioner of controlled breathing without distraction or the requirement of using chanting to concentrate on controlled breathing.

Further object and advantage is providing tangibility of meditation for users who are not familiar, or do not have the opportunity, time or money to familiarize themselves with teachings of yoga theory and learn the intricacies of yoga breathing practice. Advantage being controlled breathing.

It is a further object of the device to provide oscillation vibration, with the advantage of directly stimulating circulation in the facial and cranial areas of the body and internally massaging other parts of the body, as well as being capable of communicating and transferring vibration to another person. A further advantage being that it avoids friction and pressure on skin of traditional topical massagers hence reducing skin irritation, as well as the need for media to be applied to skin such as creams, oils or gels to facilitate transmission of vibrations from device to user.

A further object is a device which does not require electrical means to produce vibration with the advantage that it can stimulate circulation, tissues, muscles and bones.

It is a further object of the present invention to provide a respiration training system using relaxation rather than contraction of muscles with the advantage of training and providing for abdominal respiration in daily life to eliminate mental and physical stresses which result in premature ageing, its appearance and shortening duration and quality of life.

Further object is to enable controlled breathing by allowing the user to focus on breathing sound amplified by the device. Audible breathing assists with focusing for meditation, as well as use as a learning aid facilitating controlled breathing exercise patterns by assisting to maintain timing.

Further object is to facilitate a user monitoring and controlling breathing process inhalation, retention and exhalation stage, rate & duration, with the advantage that respiration cycles can be managed for improvement Still yet another object is to facilitate deep and full breathing by the user distinctly hearing inhalation and, exhalation airflow, thereby maximizing the duration of both respiration stages. The advantage being optimized breathing due to inhalation completely filling lungs with air and thereby oxygen, as well as exhalation completely emptying lungs of air and thereby carbon dioxide. A further advantage is that a user avoids shallow and irregular breathing, which sub-optimal respiration impacts the body's regulatory functions from digestion to cell regeneration;

A further object is to amplify respiration with the advantage that formerly subtle and inaudible breathing becomes amplified and audible, thereby enabling users to focus on inhalation and exhalation without distraction A further advantage being that each breathing phase can be distinguished so as to properly complete it, by fully inhaling to fill lungs with oxygen, as well as fully exhaling to empty lungs of carbon dioxide. Further advantage is that audibility assists with achieving mindful breathing and maintenance of rhythmic breathing, with the added advantage that breathing is regulated for rhythm and synchronicity. A further advantage being regulating and optimizing breathing to provide maximum oxygenation of the lungs and thereby optimal blood oxygen circulation throughout body. A further advantage being the exercise, ventilation and cleansing of lungs, stimulating cells and providing general tone and health to respiratory, circulatory and all other body organs and systems.

A further object of the device amplifying breathing is to enable teachers to train students with the advantage that it facilitates instructing and signaling to students of their current breathing state, as well as an optimal breathing state.

Further object is to amplify extremely subtle movements in the abdominal, chest and thoracic areas, with the advantage that this overcomes the difficulty of learning abdominal breathing as well as mastering yoga breathing without an expert instructor or electronic monitoring equipment present to monitor respiration.

A further object is providing optimal positioning for a user's mouth to produce 'Aum' meditation sound with the advantage of audibility and pitch of 'Aum' sound.

A further object is to provide an oxygenation device for indoor and outdoor use promoting enhanced air intake with the advantage that more effective and efficient air conditioning takes place due to the filtration of specific proximate air that is inhaled by user, not the entirety of ambient air in user's greater surrounding environment.

In conclusion, in so far as I am aware, no air filter formerly developed provides air filtration to the user, without the defect of cumbersome, inconvenient and conspicuous devices. No prior art device satisfactorily addresses both quality and quantity respiratory aspects in a relaxing method of use by a resonant cavity promoting amplified breathing facilitating focused controlled respiration, as well an vibrator providing vibration massage stimulating circulation, rather than providing a device providing emergency protection against hazardous gases, or a constraining/constrictive method for vigorous exercise pulmonary muscle training, or a plethora of attachments and devices for processing then visually or audibly signaling a user's respiration process, or providing electrically powered topical vibration unrelated to breathing.

Still further objects and advantages will become apparent from a study of the following description and the accompanying drawings.

SUMMARY

The invention, a personal air filter, has a housing comprising air filter media. The housing may also contain resonant cavity and oscillating membrane. The internal, resonant cavity (pre oscillating membrane) or external resonant cavity (post oscillating membrane) is in the form of a cylindrical bore cavity or conical bore cavity, or variation cavity. The oscillating membrane is preferably made from flexible thermoplastic such as PVC, however, other natural or artificial materials can also be used. The air filter media is preferably made from HEPA filter, however other materials can also be used. The air filter media purifies air that is inhaled by the user from the forward vent of the housing. The user holds to device to the user's mouth, using a mouthpiece, placing, the mouthpiece tip between the user's lips, for the duration of the inhalation, then either retains, or removes the device from the user's mouth for the period of retention and exhalation. This device allows the user to conveniently, comfortably and inconspicuously breathe pure air without requiring cumbersome apparatus to be inserted into the mouth between lips and gums or between teeth, or secured by or to other parts of the body such as nose, ears, or head. The user may retain the device in the mouth with or without requiring hands, using lip pressure alone for the duration of the exhalation. This also allows the user to vocalize during respiration which transduces vibration from the oscillating membrane which is also amplified by the device housing resonant cavity for transmission internally to the user's body, or externally to another person.

DRAWINGS

Figures

The foregoing and other objects of the invention will become more readily apparent by referring to the following detailed description and the appended drawings in which.

Figure 1:
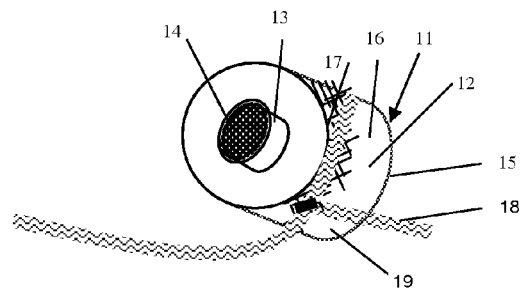
FIG. 1 is a perspective right-side view of the invented personal air filter with amplifier and vibrator constructed in accordance with the invention.

REFERENCE NUMERALS 11 device
12 housing
13 mouthpiece forward end
14 forward end vent
15 rearward end
16 housing location
17 handgrip
18 lanyard
19 cover
21 rearward end vent
24 HEPA filter media rearward screen
25 activated carbon filter media
26 HEPA filter media forward screen
28 resonant cavity
29 oscillating membrane
41 ambient air
44 user's lips
45 filtered air
48 audible resonant sound of respiration
49 oscillating vibration of vocalized respiration

DETAILED DESCRIPTION

Preferred Embodiment

In the following description, certain aspects and embodiments will become evident. It should be understood that the invention, in its broadest sense, could be practiced without having one or more features of these aspects and embodiments. It should be understood that these aspects and embodiments are merely exemplary.

FIG. 1 is a perspective view taken from the user's right side of the personal air filter with amplifier and vibrator 11 constructed in accordance with the invention. The housing 12 of the personal air filter with amplifier and vibrator 11 has a mouthpiece forward end 13, a forward end vent 14 a rearward end 15, handgrip 17, lanyard 18 and cover 19.

Figure 2:
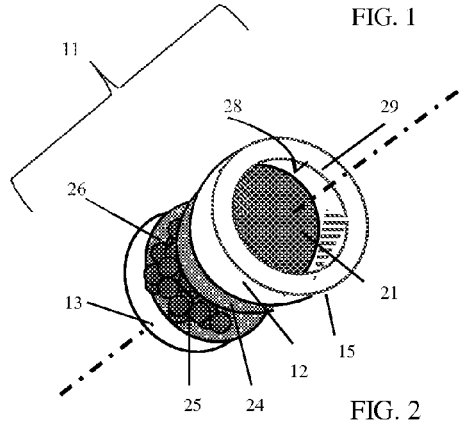
FIG. 2 is a perspective right-side exploded rearward-end view of the personal air filter with amplifier and vibrator of FIG. 1.

FIG. 2 is a perspective right-side exploded rearward-end view of the personal air filter with amplifier and vibrator showing rearward end vent 21, rearward end 15, housing 12, HEPA filter media rearward screen 24, activated carbon filter media 25, HEPA filter media forward screen 26, and mouthpiece forward end 13, resonant cavity 28 and oscillating membrane 29.

Figure 3:
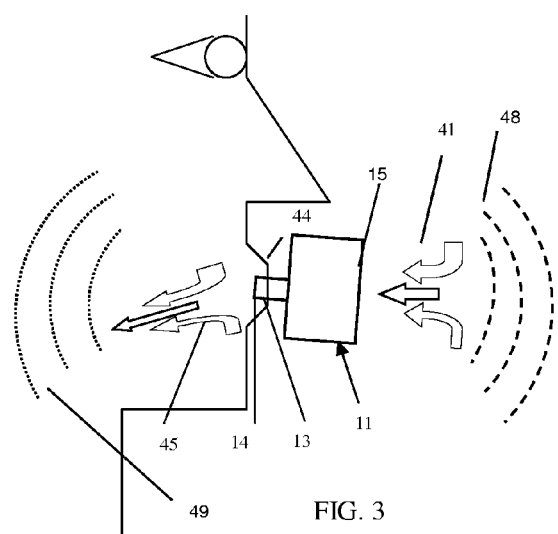
FIG. 3 is the personal air filter with amplifier and vibrator of FIG. 1 in use with mouthpiece illustrating the flow of inhaled air through the filter, resonant audible inhalation & exhalation, and oscillating vibrations of vocalized exhalation.

FIG. 3 is the personal air filter with amplifier and vibrator of FIG. 1 illustrating the flow of ambient air 41 through the device 11, the said personal air filter with amplifier and vibrator mouthpiece forward end 13 being enclosed by the user's lips 44 and filtered air 45 flowing into the user's mouth through the mouthpiece forward end vent 14 together with audible resonant sound of vocalized respiration 48 and oscillating vibration of vocalized respiration 49 transmitting to the facial and cranial area.

Operation

In operation, one uses the device 11 in a normal manner by taking it in one's hand at or near the handgrip 17 and placing mouthpiece forward end 13 in one's mouth fully enclosed by user's lips 44 and inhaling through the mouthpiece forward end 13 which forces ambient air 41 into rearward end vent 21 through the HEPA filter media rearward screen 24 activated carbon filter media 25 HEPA filter media forward screen 26 then out through the forward end vent 14. The HEPA filter media rearward screen 24, activated carbon filter media 25, and the HEPA filter media forward screen 26, are all located downstream from the resonance cavity 28 relative to inhalation air flow direction.

The device 11 is small enough that it is easily portable, being carried and concealed on the user or strapped around neck using lanyard 18. The small size of the device 11 makes it ideal for carrying in pockets, handbags or other personal means which individuals would ordinarily use on a daily basis to transport personal belongings. The device housing 12 is advantageously made from polystyrene, polyvinylchloride, polyethylene, polyethers, polycarbonate, polymethylmethacrylate, acrylonitrile butadiene styrene, polypropylene, or other plastics, with the preferred material being polypropylene. The device filter media is advantageously made from HEPA characteristic filter materials such as activated carbon granules, activated carbonmesh, activated carbon fibre, nanomaterials, nonwoven textiles or other suitable filtration materials, with the preferred material being granular activated carbon and nonwoven polypropylene. The oscillating membrane 29 is advantageously made from paper, wooden reed, flexible thermoplastic, rigid thermoplastic, other natural or artificial materials and combinations thereof, with the preferred material being polyvinylchloride shrunk over the device housing. The arrangement of the oscillating membrane 29 shrunk wrapped around the device housing 12 is also beneficial to the filtration device and amplifier in that it provides a means of retaining the filter media within the device housing 12, thus minimizing the size, weight and componentry of the device as well as providing the resonant cavity 28 for the device. The device can have different housing and filter configurations, such as different shapes, sizes and materials, such as high-carbon steel, titanium, and plastics.

In its simplest form, the personal air filter with amplifier and vibrator 11 is comprised of the device housing 12 having a mouthpiece forward end 13 and a rearward end 15. Activated carbon filter media 25 contained within the housing 12 is located between the HEPA filter media forward screen 26 and HEPA filter media rearward screen 24. The activated carbon filter media 25 is comprised between the HEPA filter media forward screen 26 and HEPA filter media rearward screen 24, which said screens allow passage of ambient air 41 from the rearward end vent 21 of the housing 12 through the mouthpiece forward end 13 and then filtered air 45 through the forward end vent 14 into the user's mouth and respiratory system. Air flow in either direction causes audible resonant sound of respiration 48 to be amplified by the resonant cavity 28, and oscillating vibration of vocalized respiration 49 to be produced by the oscillating membrane 29 which is transmitted via the user's lips to the facial and cranial area or to rest of user's body as internal massage or communicated aurally and tactilely to another person The personal air filter with amplifier and vibrator device 11, whilst it is shown as being cylindrical, or substantially cylindrical, the cross-sectional shape of the housing 12 is not essential to its function. The housing can be cylindrical, conical, or any other suitable shape. The device 11 is provided with a rearward end vent 21 that is open to the environment for ambient air entry, as well as audible resonance during inhalation and exhalation, as well as oscillation vibration during vocalized respiration 49 and a forward end vent 14, which is inserted into the user's mouth, for inhalation and ingress of purified filtered air 45.

Located within the housing 12 on either side of the activated carbon filter media 25 is a HEPA filter media rearward screen 24 and HEPA filter media forward screen 26. The said screens permit air to flow from one side thereof to the other. The said filter media screens can have different dimension, shape, or material, but are so formed as to provide HEPA characteristic air filtration and for suitable resistance to airflow through the housing 12. Depending on the type of filter material that is utilized, the said screens are sized, dimensioned and constructed accordingly, including the housing 12 permitting replaceable filter media.

Activated carbon filter media 25 is comprised within the housing 12, between the HEPA filter media rearward screen 24 and HEPA filter media forward screen 26. The activated carbon filter media 25 is selected for the anticipated application and environment in which the device will be utilized. Examples of filtration media include glass wool, cotton, activated carbon mesh, nonwoven textiles and the like. Additionally, the filtration media can be treated with an antimicrobial, antibacterial, or biocidal agent to increase the effectiveness of filtering material from the air. Additionally, the filtration media can be treated with scents, aromas or other taste inducing materials to change the characteristics or effectiveness of filtering The filtration media is dense enough to effectively filter inhaled air, can be varied to permit variable resistance to air, but not so dense that resistance to airflow is hampered. The filter media can comprise a screen alone, or if not in screen form, can be used with or without a screen for effectiveness and to prevent it from dislodging from the housing location 16. While certain filter media can be retained within the housing without application of a screen, a screen may be required with certain filtration media such as granular activated carbon filter media 25.

A handgrip 17 may be ingrained or attached to the mouthpiece forward end 13 of the housing 12, to facilitate holding of the personal air filter with amplifier and vibrator device 11 by the hand of the user or if the housing does inherently possess non-slip properties The handgrip 17 may be an engraved pattern made of the same material as the personal air filter with amplifier and vibrator device 11, or alternatively, can be made of a different, preferably softer, material so that it is more comfortable to hold. Suitable handgrip materials include silicone, neoprene, or other softer rubbers, polymers, or polymer composites.

As shown in FIG. 3, which is a schematic airflow diagram, upon inhalation, ambient air 41 is drawn into the device 11 through the rearward end vent 21 through the filtration media where it is filtered of particulates. The filtered air then passes from the filter media into the mouthpiece forward end 13, and then out through the forward end vent 14 past the user's lips 44 into the user's mouth and respiratory system. The user may remove the personal air filter with amplifier and vibrator 11 from the mouth for purposes of retention and exhalation of air, or may retain the device in the mouth between lips monitoring audible resonant sound of respiration 48 for purposes of controlling inhalation and exhalation duration, and vocalizing during exhalation for oscillating vibration of vocalized respiration 49 for purposes of internal massage or vibration communication.

The arrangement of the filter media within the housing 12 is beneficial to the filtration device in that it provides the optimal amount of resistance to flow, and thus minimizes the size of the filter media 24, 25 and/or 26 and any additional exertion by the user. The housing 12 exhibits less flow resistance, has less dead space, and thus requires less exertion by the user than other filters presently available.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

I claim:

1. A personal air filter device for use in providing a respiratory feedback when inhaling and exhaling, the filter comprising:
   (a) a housing defining a cavity and having a forward end vent and a rearward end vent, the rearward end vent being spaced apart from the forward end vent and disposed within a central opening in the housing, the forward end and rearward end vents being disposed downstream of the cavity relative to incoming air during inhalation, each vent having a first side facing the cavity, and a second side facing away from the cavity;
   (b) a mouthpiece adjacent to the second side of the forward end vent, and spaced apart from the central opening;
   (c) a cover of the housing extending from the mouthpiece to a rearward end of the housing, the cover surrounding the central opening and the cavity, the cover including an oscillating membrane adapted to oscillate at audible frequencies of a user's voice vibrations, the oscillating membrane and the cavity configured to amplify a user's voice vibrations at audible frequencies, and
   (d) a filter within the housing between the forward end and rearward end vents for filtering air passing through the housing when inhaling or exhaling, wherein the cavity resonates at audible frequencies for providing the respiratory feedback when a user exhales or inhales.

2. A personal air filter device according to claim 1, wherein the membrane comprises a thermoplastic material.

3. A personal air filter device according to claim 2, wherein the thermoplastic material extends over a portion of the housing surrounding the rearward end vent.

4. A personal air filter device according to claim 1, wherein the oscillating membrane is capable of oscillating when the user inhales or exhales.

5. A personal air filter device according to claim 1, wherein the oscillating membrane about the central opening defines an orifice having a maximum dimension, the filter having a minimum dimension that is greater than the maximum dimension of the orifice such that the filter is retained within the cavity when a user exhales.

6. A personal air filter device according to claim 1, wherein the filter includes at least one filter screen.

7. A personal air filter device according to claim 6, wherein the at least one filter screen comprises HEPA filter media.

8. A personal air filter device according to claim 6, wherein the filter comprises two filter screens with activated carbon filter media therebetween.

9. A personal air filter device according to claim 1, further comprising a lanyard.

10. A method of controlled breathing, comprising
    (a) providing a personal air filter device including a housing, a mouthpiece, a cover including an oscillating membrane covering the housing, and a filter, the housing defining a cavity and having a first forward end vent and a rearward end vent, the rearward end vent being spaced apart from forward end vent and disposed within a central opening, each vent having a first side facing the cavity, and a second side facing away from the cavity, the mouthpiece being adjacent to the second side of the forward end vent, and spaced apart from the central opening, the oscillating membrane disposed adjacent the rearward end vent and covering a portion of the central opening and covering the housing to the mouthpiece, the oscillating membrane adapted to oscillate at audible frequencies when provided with vibrations from a user's voice when the user is contacting the mouthpiece, the filter being disposed within the housing between the forward end and rearward end vents and being disposed downstream from the cavity relative to inhalation air flow direction, wherein at least one of the cavity and the oscillating membrane resonates at audible frequencies of sound for providing a respiratory feedback when a user exhales or inhales;
    (b) inserting the mouthpiece in the user's mouth;
    (c) having the user sequentially inhale through the device such that inhaled air is filtered by the device, retain breath, and exhale through the filter;
    (d) having the user adapt to a predetermined duration and rate of the user's inhalation and exhalation by having the user monitoring the audible resonant sound produced by the device during inhalation and exhalation; and
    (e) vocalizing respiration such that the oscillating membrane can produce vibrations that can be transmitted through the device to the user or another person.

11. A personal air filter device comprising
    (a) a housing defining a cavity and having a vent and a central opening opposed to and spaced apart from the vent, (b) a mouthpiece in communication with the vent,
(c) a cover that extends about the housing from proximate to the mouthpiece to at least a portion of the central opening, the cover extending about the central opening portion defining an orifice; and
(d) a filter within the cavity and being disposed downstream from the cavity relative to inhalation air flow direction, the filter having a minimum dimension that is greater than a maximum dimension of the orifice such that the filter is retained within the cavity when a user exhales;
wherein the cover comprises a plastic membrane having a periphery that defines the orifice, the periphery of the plastic membrane being adapted to vibrate at audible frequencies when a user exhales or inhales.

12. A personal air filter device according to claim 11, wherein the filter includes at least one filter screen.

13. A personal air filter device according to claim 12, wherein the at least one filter screen is HEPA filter media.

* * * * *

UNITED STATES PATENT AND TRADEMARK OFFICE
CERTIFICATE OF CORRECTION

| | |
|---|---|
| PATENT NO. | : 8,978,654 B2 |
| APPLICATION NO. | : 12/746804 |
| DATED | : March 17, 2015 |
| INVENTOR(S) | : Dimitrios Efthimiou et al. |

Page 1 of 1

It is certified that error appears in the above-identified patent and that said Letters Patent is hereby corrected as shown below:

In the claims

Column 10, Line 33, Claim 10:

After "and having a"
Delete "first"

Column 10, Line 35, Claim 10:

After "apart from"
Insert --the--

Signed and Sealed this
Twenty-third Day of February, 2016

Michelle K. Lee
*Director of the United States Patent and Trademark Office*